United States Patent [19]

Pisanu

[11] 4,340,365
[45] Jul. 20, 1982

[54] SPRAYING AND SUCTION CLEANSING DEVICE

[76] Inventor: Antonio Pisanu, Corso Vittorio Emanuele, 108, 07010 Ittiri (Sassari), Italy

[21] Appl. No.: 147,273

[22] Filed: May 6, 1980

[30] Foreign Application Priority Data

May 8, 1979 [IT] Italy .............................. 65011 A/79

[51] Int. Cl.³ ........................ A61C 5/02; A61C 17/04
[52] U.S. Cl. ......................................... 433/80; 433/91
[58] Field of Search .................... 433/100, 99, 91, 80, 433/95

[56] References Cited

U.S. PATENT DOCUMENTS 3,208,145 1/1970 Turner .
3,526,219 9/1970 Balamuth ............................. 433/91
3,735,751 5/1973 Katz .................................. 128/276
3,747,216 7/1973 Bassi et al. ........................... 433/91
3,749,090 7/1973 Stewart ............................. 128/276

FOREIGN PATENT DOCUMENTS 256175 5/1970 Switzerland .

Primary Examiner—Robert Peshock
Attorney, Agent, or Firm—Fleit & Jacobson

[57] ABSTRACT

The novel cleansing device comprises a suction pipe associated at outer and preferably concentric location with an air and/or liquid spraying tube opening adjacent the suction inlet of the suction pipe. Spraying and suction may occur at the same time.

The device can be made for odontological use, industrial or artisan use, or also for domestic uses.

10 Claims, 6 Drawing Figures

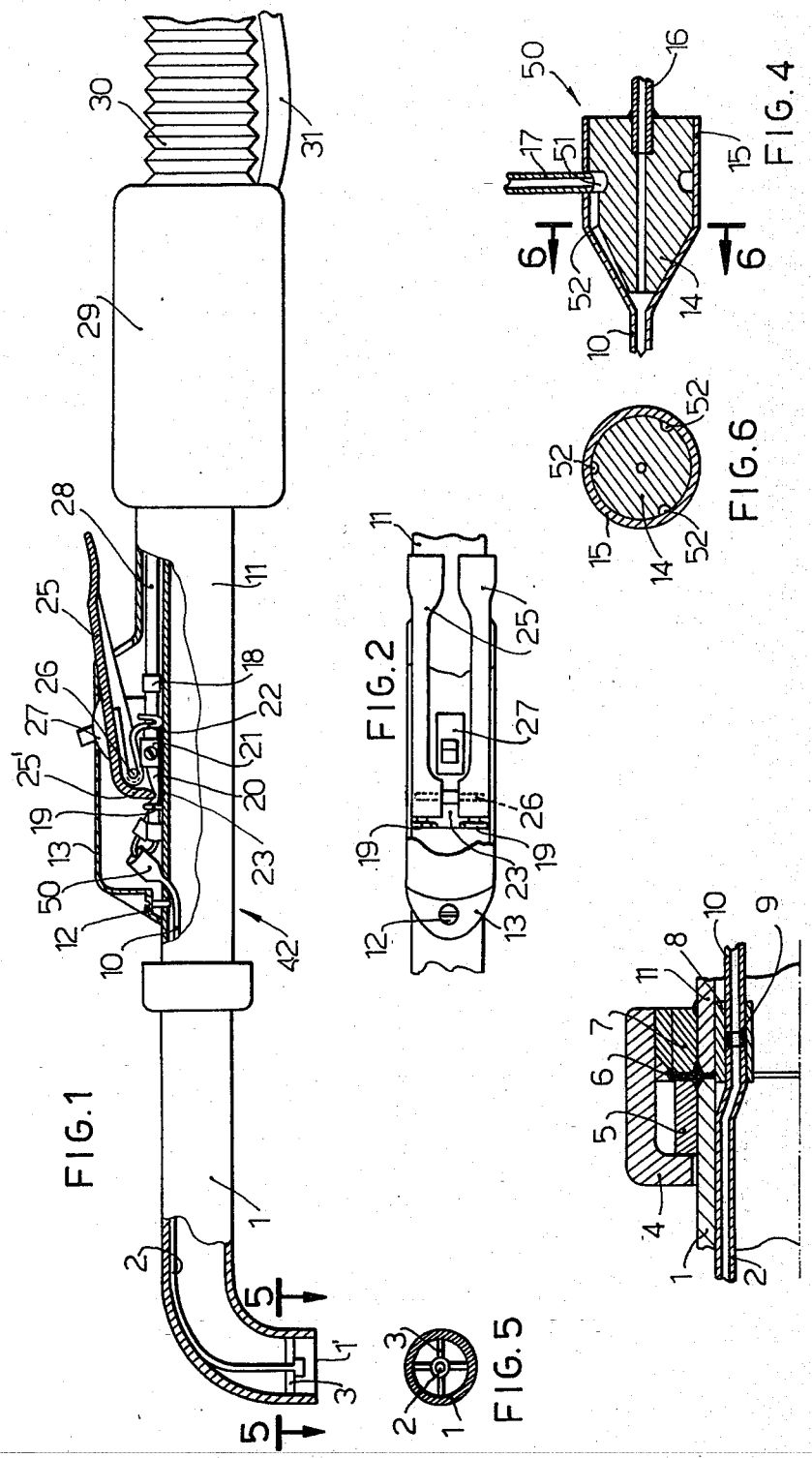

SPRAYING AND SUCTION CLEANSING DEVICE

FIELD OF THE INVENTION

This invention relates to a cleansing device operating by spray and suction, generally at a same time.

SUMMARY OF THE INVENTION

A device according to the invention comprises a suction pipe associated, at outer and preferably concentric position, with an air and/or liquid sprayer. Such an association produces an antipolluting or anticontaminating effect removing at the origin by suction both the liquid or gaseous particles as projected by the jets and repelled by the treated surface, and wastes removed by the jet action, avoiding or minimizing the dispersion thereof in the surrounding environment.

The device according to the invention will be now described with particular reference to the odontological field, while not desiring to restrict the application thereof to such a field, as it can be used in many other fields.

BACKGROUND OF THE INVENTION

The devices at present used in odontological field for the removal of wastes in the oral cavity and particularly in the dental cavity comprise an air-water spray violently moving the wastes away by projection thereof also out of the cavity in the surrounding environment, and an aspirator which by operating separately and in successive times removes the solid and liquid residual wastes. Such devices suffer from the following disadvantages: the violent spray action, by outwardly projecting fragments or pieces of dentine, of bacterial plaque, causes a serious pollution or contamination by spreading in the surrounding environment corpuscules and powders of high bacterial charge. The action of the aspirator acting separately and in successive times is limited to collect the remaining solid and liquid material in the oral cavity without avoiding the scattering of the above mentioned material. It is the object of the present invention to overcome such disadvantages.

OBJECTS OF THE INVENTION

The invention consists of a device capable of simultaneously providing a suction and spray action, such a device comprising a suction pipe with a suction inlet, and internally thereof a spray tube opening adjacent the suction inlet. The invention has the following advantages:

(a) possibility of cleaning the oral and dental cavity with spray or air only, without contaminating the surrounding environment;
(b) possibility of enhancing the suction effectiveness mobilizing by the jet and admitting into the sucking flow those wastes that otherwise could not be reached; and
(c) the possibility of effecting by the same device and engagement of only one hand both of the spray and suction operations requiring at present two distinct apparatuses or devices.

A possible embodiment of the invention is shown by mere way of example in the accompanying drawings, in which:

In the drawing:

FIG. 1 is a longitudinal sectional view with portions broken away and shown in section showing a device embodying the inventive concept;

FIG. 2 is a top view showing only the switch and microvalve unit;

FIG. 3 is an enlarged axial sectional view showing the detail for the sprayer spout attachment to the handle means;

FIG. 4 is an enlarged cross-sectional longitudinal view showing the sprayer mixer;

FIG. 5 is a sectional view taken along line 5—5 of FIG. 1; and

FIG. 6 is a sectional view taken along line 6—6 of FIG. 4.

DESCRIPTION OF A PREFERRED EMBODIMENT

Referring to the accompanying drawings, reference numeral 1 denotes a suction spout or intake pipe, formed of a pipe curved at the end where it forms the suction inlet 1' (but it could be straight or of different angling); at the other end the pipe has a shoulder 5 (see FIG. 3), on which a ring nut 4 bears and screws down on a threaded ring 7 welded to a metal pipe 11 of the handle means.

Reference numeral 2 indicates a tube length of a sprayer which, adjacent the suction inlet 1' is positioned by a centering device 3 welded to pipe 1, while adjacent the attachment to the handle means is welded to pipe 1, and is offset from the inner surface of the latter for engagement with a further length 10 of the sprayer tube, which has a small ring 8 welded guiding the end of tube 2 and internally containing a sealing ring 9, whereas reference numeral 6 indicates the sealing ring for the spout.

At one end the valve cover or housing 13 is fixed on the handle of the handgrip 29 and is secured at the other end on pipe 11 by means of a screw 12.

The sprayer can deliver or dispense air, or a liquid, or preferably a liquid mixed with air.

Reference numerals 14 through 17 indicate the parts making up a mixer 50, that is, the mixer body 14 on which a small hole is axially drilled, to which the liquid flows through capillary 16, and on the outer surface a groove 51 having some longitudinal splines 52 of decreasing section diverting therefrom; a jacket or liner 15, in which said body 14 is perfectly accomodated; microconduits are formed between said jacket or liner and body, on which the compressed air flows from capillary 17 and is distributed by the groove on the body; by coming into collision with the liquid jet, the air will cause a finely atomized mixture.

Reference numeral 20 indicates two lengths of special rubber conduit or hose, one of which having the liquid passing therethrough, and the other the compressed air; at one side the two hoses engage on the capillaries 16 and 17, respectively, and at the other side on the liquid and compressed air supply conduits respectively. Sealing is assured by clamping rings 18. These hoses 20 must be highly flexible and fully squeezable by applying a much limited force.

Reference numeral 25 indicates the levers for the pushbutton shut off valves 25', which are pivoted on said valve cover or housing 13 by a pin 26; they are in the shape of a "hoe" and kept pressed against a block 23 by means of springs 22; inserted between said lever and block, which is welded to the valve cover or housing 13, are the rubber hoses 20, maintained at correct position by U-bolts 19. Reference numeral 21 indicates two screw clamps acting as control valves for air and liquid, respectively, whereas reference numeral 27 indicates the drive microswitch for the aspirator situated between said levers 25 and secured to said block 23.

Reference numeral 29 indicates the handle of the handgrip, which handle is made of two shells which are clamped by screws or the like on pipe 11, while reference numeral 30 indicates a flexible conduit of the aspirator which is connected to pipe 11, and 31 the cable containing two conduits 28 for air and pressurized liquid and two small cables 32 for the microswitch 27.

As it will be appreciated, the device is preferably made of two parts, that is, one part 40 comprised a first length of the suction pipe 1 with the suction inlet and length 2 of the sprayer tube, and the second part 42 comprises the handgrip 29 of the device with a second length 11 of the suction pipe and a second length 10 of the sprayer tube.

Of course, the constructive solution of the individual details and the location or arrangement thereof may vary from those as described and shown, but without departing from the scope of the invention.

For instance, the mixer could be located adjacent the suction inlet, control or pushbutton shut off valves of the needle or male type could be adopted, or electrovalves inserted at the bottom of the flexible headers or manifolds and hiving the drive switches inserted in the handgrip, and so on.

What I claim is:

1. A spray and suction cleansing device comprising:
   means for defining an elongate housing having a suction pipe with a terminal suction opening at an end thereof;
   means for supplying negative pressure through said suction pipe to said terminal suction opening for removing materials from a surface being cleansed;
   a mixer supported by said housing having a mixer body and a liner in sealing contact with an outer circumferential surface of the mixer body, the mixer body having an axially extending bore with an inlet end and an outlet end, a circumferentially extending groove radially spaced from the bore, and a second groove formed in the circumferential surface interconnecting the circumferentially extending groove with a space adjacent the outlet end of said bore and having a decreasing cross sectional area in a direction extending towards the space;
   a first tube having an inlet connectable to a source of cleansing liquid and an outlet in fluid communication with said inlet end of said bore for supplying cleansing liquid to said mixer body;
   a second tube having an inlet connectable to a source of pressurized gas and an outlet in fluid communication with said circumferentially extending groove for supplying pressurized gas to said mixer body, the supplied gas flowing from the circumferentially extending groove through the second groove into the space adjacent the outlet end of said bore and pressurizing the cleansing liquid;
   lever means disposed intermediate the inlet and the outlet ends of said first and said second tubes for controlling the supply of pressurized gas and cleansing liquid to said mixer body; and
   a third tube extending between the space adjacent the outlet end of said bore and said terminal suction opening and having a terminal spraying opening for supplying pressurized cleansing liquid to the surface being cleansed so that the liquid loosens substances from the surface for removal by said means for supplying negative pressure, said third tube being encompassed by said suction pipe so that the portion of said suction pipe adjacent said terminal suction opening tends to prevent dispersion of said cleansing liquid thereby facilitating its removal from the surface being cleansed by said means for supplying negative pressure.

2. A device according to claim 1, wherein said lever means comprises a control valve and a shut off valve associated with each of said first and said second tubes, and a lever for moving said control valve, said device further comprising a drive switch for controlling the means for supplying negative pressure.

3. A device according to claim 2 characterized in that said shut off valves comprise electrovalves located at the bottom of the flexible conduits and controlled by pushbutton switches inserted in a handgrip of the device.

4. A device according to claim 1, characterized by said housing comprising two parts connectable to each other, the first part comprising a first length of the suction pipe with the terminal suction opening and internally a length of said third tube, the second part comprising a handgrip for the device with a second length of the suction pipe and a second length of the third tube, sealing rings being interposed between said two parts, said two parts of the device being connected by means of a threaded ring nut.

5. A device according to claim 1 for odontological use.

6. A device according to claim 1 for surgical use, wherein the end of the device has a suitable shape for the disinfection of tissues or cavities, and the device being also prearranged for use with one or more cleaning or disinfecting liquids.

7. A device according to claim 1 for industrial use, wherein the liquid used may be air, water, solvents, lubricants and the like for cleaning, deterging, lubricating surfaces in artisan or industrial activity.

8. A device according to claim 1 for domestic cleaning use, characterized in that said sprayer is an air sprayer.

9. A device as claimed in claim 1 wherein said terminal spraying opening lies in a plane containing said terminal suction opening.

10. A device as claimed in claim 1 wherein said terminal spraying opening is disposed upstream with respect to a plane containing said terminal suction opening.

* * * * *